United States Patent
Marcoux

(10) Patent No.: US 8,414,502 B2
(45) Date of Patent: Apr. 9, 2013

(54) SYSTEM AND METHOD FOR THE OBJECTIVE MEASUREMENT OF HEARING ABILITY OF AN INDIVIDUAL

(75) Inventor: Andre Marcoux, Ottawa (CA)

(73) Assignee: Widex A/S, Lynge (DK)

( * ) Notice: Subject to any disclaimer, the term of this patent is extended or adjusted under 35 U.S.C. 154(b) by 523 days.

(21) Appl. No.: 12/564,024

(22) Filed: Sep. 21, 2009

(65) Prior Publication Data
US 2010/0076339 A1    Mar. 25, 2010

Related U.S. Application Data

(63) Continuation-in-part of application No. PCT/DK2007/000145, filed on Mar. 23, 2007.

(51) Int. Cl.
*A61B 5/00* (2006.01)
*A61B 1/227* (2006.01)
*H04R 25/00* (2006.01)

(52) U.S. Cl. .................. 600/559; 600/544; 381/312

(58) Field of Classification Search .................. 600/544, 600/559; 381/312
See application file for complete search history.

(56) References Cited

U.S. PATENT DOCUMENTS

| | | | |
|---|---|---|---|
| 4,275,744 A * | 6/1981 | Thornton et al. | 600/544 |
| 4,493,327 A | 1/1985 | Bergelson et al. | |
| 5,813,993 A * | 9/1998 | Kaplan et al. | 600/544 |
| 5,999,856 A | 12/1999 | Kennedy | |
| 6,080,112 A * | 6/2000 | Don | 600/559 |
| 6,236,884 B1 * | 5/2001 | Hunter et al. | 600/544 |
| 6,236,885 B1 * | 5/2001 | Hunter et al. | 600/545 |
| 6,658,122 B1 | 12/2003 | Westermann et al. | |
| 2001/0034493 A1 * | 10/2001 | Stone | 600/559 |
| 2004/0116151 A1 * | 6/2004 | Bosch et al. | 455/550.1 |
| 2004/0204659 A1 | 10/2004 | John et al. | |
| 2005/0131272 A1 | 6/2005 | Waldmann | |
| 2008/0262371 A1 * | 10/2008 | Causevic | 600/544 |

FOREIGN PATENT DOCUMENTS

| | | |
|---|---|---|
| EP | 1 133 898 B1 | 8/2002 |
| EP | 1089659 B1 | 7/2004 |
| JP | 2001511673 A | 8/2001 |
| JP | 2002503972 A | 2/2002 |
| JP | 2003533258 A | 11/2003 |
| WO | WO 9704704 A1 | 2/1997 |
| WO | WO 9836711 A1 | 8/1998 |
| WO | 0044198 A1 | 7/2000 |
| WO | WO 0187147 A2 | 11/2001 |

OTHER PUBLICATIONS

Office Action for JP2009553907 dated Sep. 20, 2011, with English translation.

* cited by examiner

*Primary Examiner* — Sean Dougherty

(74) *Attorney, Agent, or Firm* — Sughrue Mion, PLLC

(57) ABSTRACT

A system for determining the hearing ability of an individual comprises a generator for generating a test stimulus signal, a hearing aid (2) having a digital signal processor for processing said test stimulus signal and converting it in order to output an acoustic stimulus signal, and a first synchronizing means. The system further comprises an electrophysiological instrument (1) having a second synchronizing means, and means (7) for establishing from said individual an evoked response to said acoustic signal. The first synchronizing means and said second synchronizing means exchange a synchronization signal in order to synchronize said evoked response to said acoustic stimulus signal. The invention also provides a hearing aid and a method for carrying out electrophysiological measurement of the hearing ability of an individual.

10 Claims, 3 Drawing Sheets

SYSTEM AND METHOD FOR THE OBJECTIVE MEASUREMENT OF HEARING ABILITY OF AN INDIVIDUAL

RELATED APPLICATIONS

The present application is a continuation-in-part of application No. PCT/DK2007000145, filed on Mar. 23, 2007, in Denmark and published as WO 2008116462 A1.

BACKGROUND OF THE INVENTION

1. Field of the Invention

The present invention generally relates to the field of assessing hearing capacity in human beings. The invention, more particularly, relates to systems and methods for determining the hearing ability of an individual by providing an acoustic stimulus in combination with electrophysiological threshold measurement techniques. The invention, still more specifically, relates to systems and methods for determining the hearing ability of an individual through the application of an acoustic stimulus provided by a hearing aid.

Newborn hearing screening programs typically recommend that newborn infants who have failed an initial hearing screening test be sent for a complete hearing assessment prior to their 3-month anniversary. However, since children are unable to produce appropriate motor responses, which are typically required for the behavioral hearing assessment, an objective estimation of hearing is imperative. This objective estimation can be provided by electrophysiological means and has shown excellent correspondence with behavioral thresholds collected later in life. One such electrophysiological test is termed the Auditory Brainstem Response (ABR).

The ABR primarily consists of five waves, labeled I to V, which represent the evoked synchronous activity generated by the auditory nerve and the brainstem. The ABR is evoked by short-duration auditory stimuli with short rise times such as auditory clicks or tone bursts. In order to obtain a waveform that can be interpreted, the evoked response is generally recorded for 15 to 25 ms following onset of the auditory stimulus, averaged over thousands of trials and filtered to eliminate unwanted neuro-muscular or environmental electrical activity. The ABR is recorded from electrodes, which are strategically placed on or in the vicinity of the forehead and mastoids, creating differentials in potential (i.e. dipoles). The evaluation of latency, amplitude and morphology of the ABR wave V will assist the audiologist in determining hearing ability or threshold of the individual. The ABR threshold is associated with the lowest level of auditory stimulation capable of evoking a visible or detectable wave V.

Another frequently used electrophysiological test is the Auditory Steady-State Response (ASSR). The ASSR relies on modulating a pure-tone, either in frequency or amplitude, and presenting this modulated tone to the ear of the patient at various intensities. The ASSR consists of a statistical averaging which determines whether the tone modulation is also represented in the continuous encephalographic activity. Unlike the ABR, the ASSR does not require a time-locked averaging to the onset of the acoustic stimulus, as the modulation and hence the occurrence of the modulation is steady-state. The statistical presence of the modulation at various levels will assist the audiologist in determining hearing ability or threshold of the individual. The ASSR threshold is associated with the lowest level of auditory stimulation capable of evoking its attributed modulation within the measured neural activity.

2. Prior Art

EP-B1-1089659 shows a method for determining an auditory brainstem response (ABR) to an acoustic stimulus in a human test subject.

EP-B1-1133898 teaches a hearing aid for in-situ fitting, where an audiogram is measured with the hearing aid placed in the ear and acting as an audio signal source.

In-situ audiometry has been documented to reduce variability otherwise associated in using one transducer to couple audiometric equipment to the child's outer ear during the evaluation phase and another transducer used to couple the hearing aid to the child's outer ear during the amplification phase. In so doing the coupling and/or tubing and/or venting properties of each transducer are difficult to estimate during the calculation of output characteristics for the child's hearing aid in relation to the measured hearing loss. There is therefore a significant advantage of using the same coupling system and identical transducer both for the evaluation of hearing loss and the subsequent calculation of output characteristics for the hearing aid, such as prescribed by an in-situ technique.

At the present time, there are several ABR and ASSR equipments on the market. These equipments both deliver the acoustic signals to the individual's ears using headphone or insert earphone transducers and collect and manipulate the electrical activity generated by the auditory nerve and brainstem.

While these tools are useful in determining the unaided thresholds of children and adults, they are somewhat limited in their applicability towards common intervention or treatment practices in two important ways: a limitation to determine an aided threshold and a limitation to consider the disparity between the influence of the transducers used in the evaluation and treatment phases of an intervention with a hearing-impaired individual.

Aided thresholds reveal important information to the audiologist as they reveal the softest sound that a child is able to detect when aided by his/her hearing aid. From this information, an audiologist is able to determine whether a young child is adequately fit with an appropriate hearing device for the purposes of hearing the softest elements of speech that will permit the child of developing an acceptable level of language. While it is possible to obtain the aided thresholds from older children using traditional behavioral methods, it is impossible to obtain this information from very young children. While it would be possible to measure aided threshold using an electrophysiological technique such as ABR and ASSR, these would entail delivering acoustic stimuli in the free field. Free field measurements possess inherent limitations when testing infants and toddlers, such as ensuring a fixed positioning of the head and torso during the entire duration of the measurement; a task quite difficult to achieve in the pediatric population. It would be very useful for an objective, electrophysiological methodology to assist with the estimation of aided thresholds in this capacity, without the limitations imposed by free-field measurements.

When applying an electrophysiological method for measuring the hearing threshold of a baby or a young child, it should preferably be asleep; otherwise signals may arise due to neuron-muscular activity, and interfere with the auditory evoked potentials sought. As such, the measurements may not reflect the supposed evoked auditory responses. Furthermore, when an electrophysiological threshold measurement is carried out in a free field, there is an uncontrolled variation of about 10 dB to 20 dB.

SUMMARY OF THE INVENTION

It is a preferred feature of the invention to provide a system that is less sensitive to the movements of the individual to be tested when measuring the aided threshold than is currently possible with free-field techniques.

It is another preferred feature to reduce the variability in an electrophysiological threshold measurement.

The invention, in a first aspect, provides a system for determining the hearing ability of an individual, comprising a generator for generating a test stimulus signal, a hearing aid, said hearing aid having a digital signal processor for processing and converting said test stimulus signal in order to output an acoustic stimulus signal, and a first synchronizing means for emitting a synchronization signal, and an electrophysiological instrument, said instrument having a second synchronizing means and means for establishing from said individual an evoked, electrophysiological response to said acoustic stimulus signal, wherein said hearing aid is adapted to operate with an essentially constant time delay between emitting said synchronization signal and outputting said acoustic stimulus signal, and wherein said first synchronizing means and said second synchronizing means are adapted to exchange said synchronization signal in order to synchronize said evoked response to said acoustic stimulus signal thereby relating an evoked response from the individual in response to the acoustic stimulus signal emitted from the hearing aid.

The electrophysiological instrument is an instrument for determining an evoked response to an acoustic signal, such as an ABR or an ASSR. The means for generating a test stimulus signal could comprise a look-up table of test wave samples of various characteristics with respect to intensity, modulation, frequency, duration, and envelope characteristics such as rise/fall times. These characteristics would be chosen from the lookup table to construct stimuli that are currently recommended for various electrophysiological measurement protocols, such as, but not limited to, clicks, tone burst, tone pips and chirps for the ABR, as well as frequency and amplitude-modulated tones for the ASSR. As such the signal generator would have the potential of generating any acoustic stimulation required for a specific electrophysiological measurement protocol.

The hearing aid could be based on any kind of standard hearing aid, such as a behind-the-ear hearing aid, an in-the-ear hearing aid or a completely-in-the-canal hearing aid, with modifications according to the invention.

In an embodiment, the combination of said generator, said digital signal processor and said converting means is calibrated to achieve a well-defined acoustic stimulus signal.

In another embodiment the system comprises a fitting system. It is an advantage to provide a fitting system that may control the audiological test, since the fitting system can be used in a later tuning of the hearing aid parameters. The fitting system may comprise the first synchronizing means, and the fitting system may further comprise a generator for generating a test stimulus signal.

In an embodiment, the hearing aid further comprises the first synchronizing means and the generator for generating a test stimulus signal.

In another embodiment the system is adapted to operate with a time delay of less than 50 micro seconds.

The invention, in a second aspect, provides a hearing aid comprising a generator for generating a test stimulus signal, a digital signal processor adapted for processing and converting the test stimulus signal in order to output an acoustic stimulus signal, and a first synchronizing means for providing timing information about the outputting of the acoustic stimulus signal, wherein said digital signal processor is adapted to process the test stimulus signal according to an audiologic fitting prescription for an individual, in order to test the aided hearing threshold of the individual.

The invention, in a third aspect, provides a system for determining the hearing ability of an individual, said system comprising, an electrophysiological instrument, said instrument having means for generating a test stimulus signal and electrophysiological response means for establishing from said individual an evoked response, a hearing aid, said hearing aid having a calibrated input adapted for receiving said test stimulus signal, and a digital signal processor for processing and converting said test stimulus signal into an acoustic stimulus signal suitable for evoking in the individual an electrophysiological response, wherein said hearing aid is adapted for operating with a constant time delay between receiving the test stimulus signal and outputting the acoustic stimulus signal.

The invention, in a fourth aspect, provides a method for carrying out electrophysiological measurement of the hearing ability of an individual, comprising the steps of generating a trigger pulse, generating in said hearing aid, in response to said trigger pulse, a test stimulus signal and converting the test stimulus signal into an acoustic stimulus signal, wherein the time delay between the trigger pulse and the acoustic stimulus signal is essentially constant, and measuring an electrophysiological response evoked in the individual by the acoustic stimulus signal.

BRIEF DESCRIPTION OF THE DRAWINGS

Other aspects and advantages of the present invention will become clear from the following detailed description taken in conjunction with the accompanying drawings, which illustrate, by way of example, the principles of the invention.

In the drawings.

DETAILED DESCRIPTION OF THE INVENTION

Figure 1:
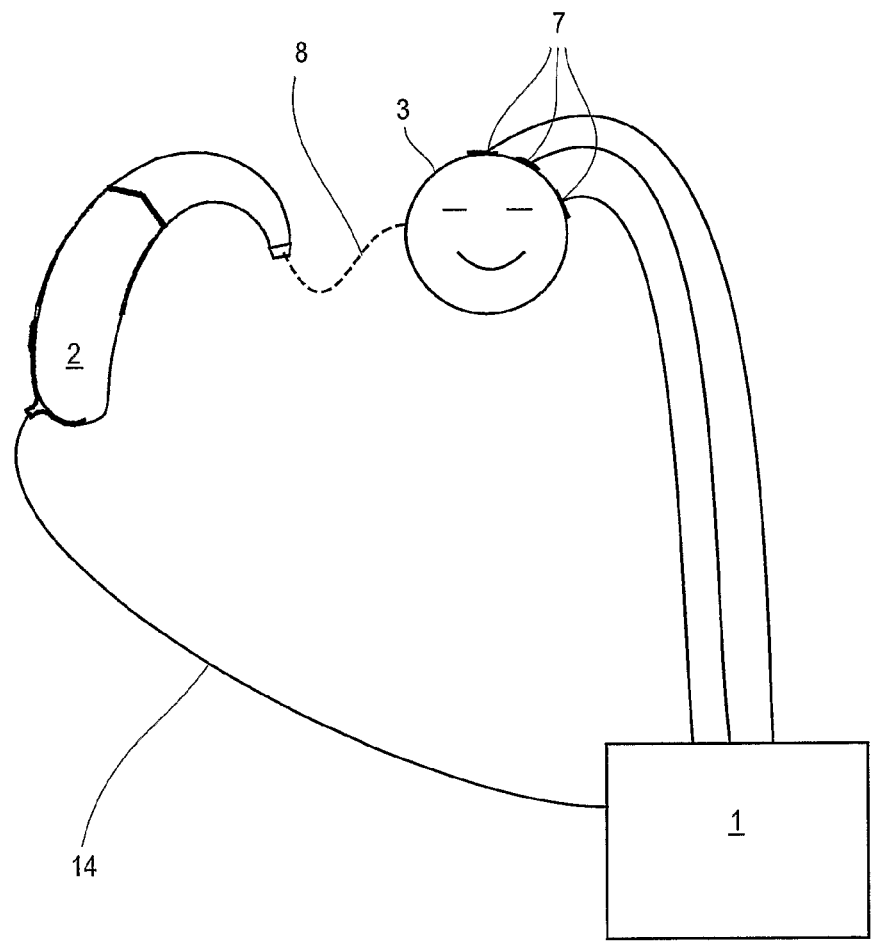
FIG. 1 shows a system for determining the hearing ability of an individual.

FIG. 1 shows a system for determining the hearing ability of an individual 3. The system comprises an electrophysiological instrument 1 such as an instrument adapted to perform an ABR or an ASSR, a hearing aid 2 that is connected to the electrophysiological instrument 1 by a cable 14, and a number of electrodes 7 that are placed on the head of the individual 3 to have his or her hearing ability determined. The electrodes 7 are connected to the ABR instrument and serve to sample fluctuations of electric potentials evoked by an auditory response to a stimulus signal so the electrophysiological reaction can be determined by use of the ABR or ASSR instrument 1. The hearing aid 2 emits acoustic stimulus signals 8 that the individual 3 may register. In setups according to the prior art, the ABR or ASSR instrument 1 is usually connected to a set of headphones that generates auditory signals to the person to be tested. However, according to the invention the auditory stimulus signals are emitted by the hearing aid 2.

Figure 2:
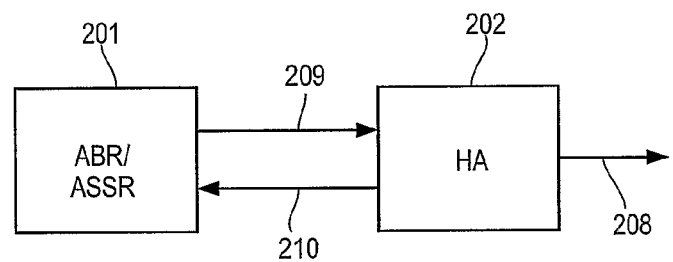
FIG. 2 shows a hearing aid interacting with an electrophysiological instrument.

In one embodiment of the invention, shown in FIG. 2, a hearing aid 202 interacts with an electrophysiological instrument 201 such as an ABR or an ASSR equipment 201. The hearing aid 202 receives a trigger pulse 209 from the ABR equipment 201 and the hearing aid generates synchronization signals 210 in return that are used to ensure that the electrophysiological reaction can be measured at a constant time delay.

Figure 3:
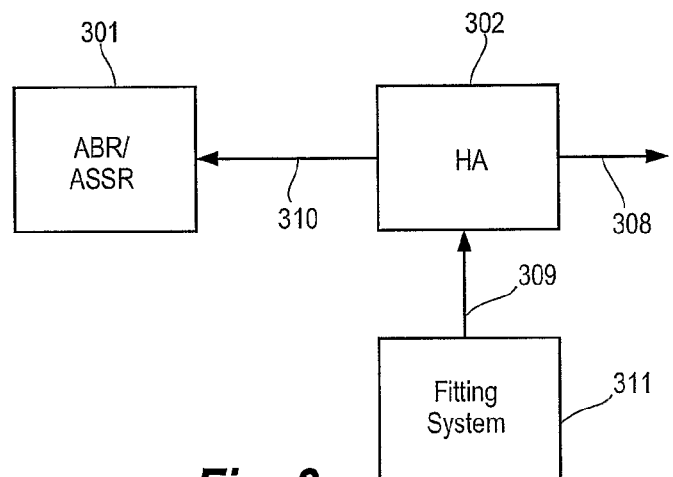
FIG. 3 shows a hearing aid interacting with an electrophysiological instrument and a fitting system.

In FIG. 3 another embodiment according to the invention is shown. In the Fig. a fitting system 311 is connected to the hearing aid 302. In this set up the fitting system controls the hearing aid 302 so that it is set in a linear enhancement mode. The fitting system 311 initiates the test procedure, e.g. by sending a trigger pulse 309 to the hearing aid 302, and the hearing aid 302 generates an acoustic stimulus signal 308 and sends a synchronization signal 310 to the ABR or the ASSR equipment 301.

Figure 4:
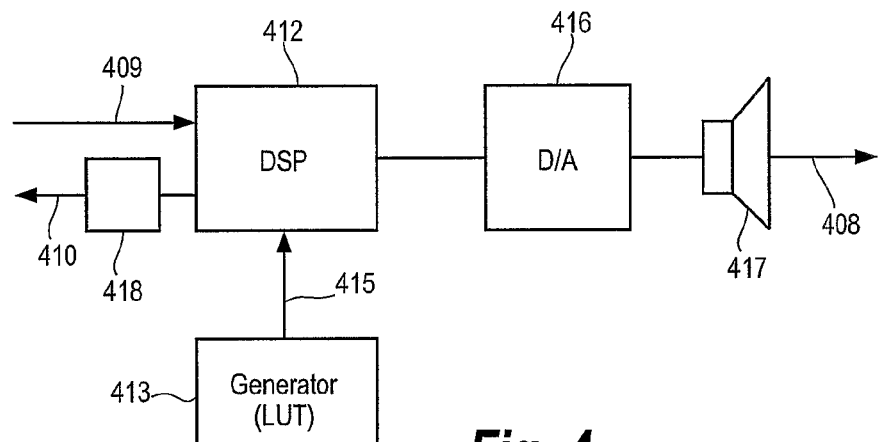
FIG. 4 shows a hearing aid according to an embodiment of the invention.

FIG. 4 shows an embodiment of a hearing aid that can be used in the setups illustrated in FIG. 2 and FIG. 3. The hearing aid comprises a Digital Signal Processor DSP 412 that is adapted to receive a trigger pulse 409, either from the ABR equipment or from the fitting system. In response to the trigger pulse 409 the DSP 412 emits a first synchronization signal 410 via a synchronization means 418 to the ABR equipment. In another embodiment the first synchronization means 418 is integrated into the DSP 412. The DSP 412 retrieves a test signal 415 from a generator 413, e.g. by reading a wave sample from a look up table 413. In a particular embodiment, the generator is integrated into the DSP 412. The test signals 415 are processed by the DSP 412 and emitted via a D/A converter 416 through an output transducer 417, such as a loudspeaker, as an acoustic stimulus signal 408.

Figure 5:
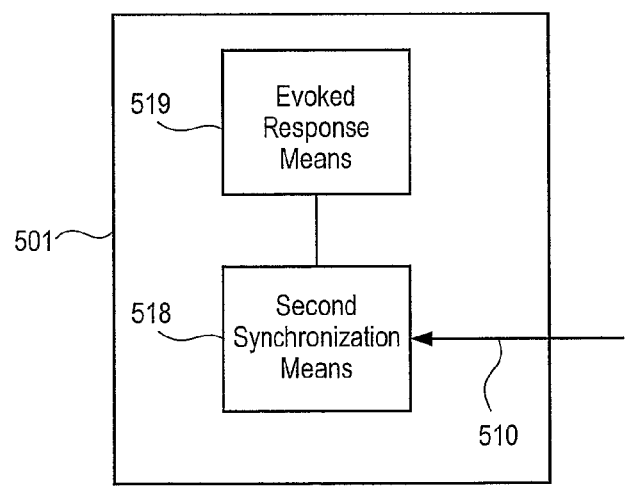
FIG. 5 shows an electrophysiological instrument for the system according to the invention.

FIG. 5 shows an ABR 501 that comprises evoked response means 519 for establishing an evoked response from the individual being tested. The evoked response means 519 is connected to a second synchronization means 518 such that when the second synchronization means 518 receives a synchronization signal 510, the evoked response means 519 knows when to start measuring the evoked response. The first synchronizing means 418 in the hearing aid in FIG. 4 and the second synchronizing means 518 in the ABR in FIG. 5 are arranged to exchange a synchronization signal in order to relate an evoked response from the individual being tested in response to the acoustic stimulus signal 408 emitted from the hearing aid.

It is crucial that the time delay from the instant a synchronization signal is received by the ABR until the acoustic stimulus signal is emitted from the hearing aid is approximately constant, or at least known, in order to obtain a reliable estimation of the auditory response. The evoked response is averaged over thousands of samples and filtered to eliminate unwanted neuro-muscular or environmental electrical activity, and thus it is important that all the evoked responses are sampled with the same starting point so uncertainty related to the starting point is minimized.

In one embodiment the hearing aid is adapted to operate with a time delay between the synchronization signal and the acoustic stimulus signal that is less than 50 micro seconds. Any variations below that limit may be acceptable. However, in an advanced DSP-based hearing aid, the DSP performs a number of tasks, such as basic processing for hearing deficiency compensation, estimating the acoustic feedback path, estimating the directivity pattern of the current sound environment and controlling the compression mechanism, which tasks all consume noticeable processing time. Depending on the programming architecture, these tasks, except for the basic one, are likely to involve adaptive processing. Tasks that involve adaptive processing may give rise to varying processor delays. Therefore, in an advanced adaptive hearing aid, synchronization is no trivial matter.

According to an embodiment of the invention the processor is adapted for creating a constant delay mode suitable for testing, wherein the adaptive processes are stalled while signals originating from the ABR equipment will be processed with a constant time delay. Alternatively, if some of the active processes are known to cause varying time delays in the DSP, such known variations could be taken into account in the synchronization, e.g. by the ABR equipment, in order that the evoked responses are sampled at the approximately the same time. Still another way could be to let the DSP control that the acoustic stimulus signal is emitted after a constant time period despite that it incurs different time delays to process the stimulus signal. In yet another embodiment the hearing aid sends a synchronization signal to the ABR equipment such that it can start sampling the evoked response at the same starting point.

As with any type of instrument used to present acoustic stimuli to the ear, a calibration is required to ensure that a predetermined level of sound pressure level can be measured in a standard coupler when the equipment is placed at the audiometric zero. The amount of sound pressure level corresponds to that documented as required to elicit perception of the specific stimulus in a group of young, normal-hearing adults. From this point, a calibration must also ensure that increments of the instrument's intensity dial should follow identical increments in sound pressure level as measured in the appropriate standard coupler. A calibration, and hence a relation between sound pressure level and the instrument's audiometric zero must be made for every type of stimulus, across frequencies. Furthermore, calibration must be performed for every type of transducer which the equipment permits to couple to the individual's ear during a hearing assessment.

Testing children requires an amendment of this calibration in order to reveal pertinent audiometric (threshold) information. This amendment is due to the fact that the outer ear of the child is immature during the first 5 years of life, and hence transforms sounds on their way to the eardrum in a manner that is different from that measured in adults. As such, different amounts of sound pressure level are necessary to elicit perception in young children and hence the relationship between sound pressure level and an instrument's audiometric zero devised during calibration, has no functionality when testing a young child. Unless the calibration is amended, threshold values obtained from a testing equipment will not reflect the young child's hearing status at several, if not all, test frequencies. This is particularly important for ABR and ASSR as these threshold measurement techniques are mostly carried out with children under the age of 6 months.

While it could be possible to calibrate hearing testing equipment for children, the maturation process which occurs at the level of the young child's outer ear during the first 5 years is much too rapid and hence impossible to capture using a single calibration measurement. However, there are two ways of re-establishing a correspondence between sound pressure level and a testing equipment's audiometric zero. First, a correction can be applied to consider the influence of the child's outer ear properties in order to provide meaning to threshold values collected during ABR and ASSR measurements. These corrections, such as the RECD for insert phones and hearing aids, have been widely described in the literature and are commonly obtained, either by means of an individual measurement from a child's outer ear using a probe-microphone system, or by means of an age-appropriate estimation reported from the literature. As second way of re-establishing correspondence between sound pressure level and audiometric zero is to permit real-ear calibration prior to testing. Using a probe-microphone, either directly integrated within a hearing aid, or from a separate equipment with probe-microphone capabilities, placed at the eardrum of the child, the hearing aid is able to generate the stimuli to be used during the evaluation and determines the correspondence between the ABR or ASSR equipment's intensity dial and the sound pressure level measured at the child's eardrum. The equipment's audiometric zero is reset as to produce the exact amount of eardrum sound pressure level as documented in the literature to elicit perception of that stimulus in a group of normal-hearing individuals Before the arrangement can be used, the hearing aid is calibrated, either on location or in advance, by measuring the auditory signal emitted by the hearing aid. The test can then be carried out e.g. with a series of auditory signals of varying frequencies in the interval 500 Hz to 4000 Hz and of varying loudness in the interval 0 dB up to 120 dB, in order to measure the hearing threshold level of the person to be tested as in a normal ABR or ASSR test.

The calibration of the ABR or ASSR equipment in combination with the hearing aid can be carried out according to the standard 711 IEC. For further details regarding the integration of a probe microphone in a hearing aid reference may be had to U.S. Pat. No. 6,658,122, the contents of which are incorporated hereinto by reference.

I claim:

1. A system for determining a hearing ability of an individual, comprising
    a generator for generating a test stimulus signal,
    a hearing aid of a type selected from the group consisting of a behind-the-ear hearing aid, an in-the-ear hearing aid and a completely-in-the-canal hearing aid, said hearing aid having a digital signal processor for processing and converting said test stimulus signal in order to output an acoustic stimulus signal, and a first synchronizing means for emitting a synchronization signal, and
    an electrophysiological instrument, said instrument having a second synchronizing means and means for establishing from said individual an evoked, electrophysiological response to said acoustic stimulus signal,
    wherein said hearing aid is adapted to operate with an essentially constant time delay between emitting said synchronization signal and outputting said acoustic stimulus signal, and
    wherein said first synchronizing means and said second synchronizing means are adapted to exchange said synchronization signal in order to synchronize said evoked response to said acoustic stimulus signal, the synchronization of the signal relating an evoked response from the individual in response to the acoustic stimulus signal emitted from the hearing aid.

2. The system according to claim 1, wherein the combination of said generator, said digital signal processor and said converting means, is calibrated to achieve a well-defined acoustic stimulus signal.

3. The system according to claim 1, comprising a fitting system connected to the hearing aid.

4. The system according to claim 3, wherein the first synchronizing means is integrated into said fitting system.

5. The system according to claim 3, wherein the generator is integrated into said fitting system.

6. The system according to claim 1, wherein said first synchronizing means and said generator are integrated into the hearing aid.

7. The system according to claim 1, wherein the constant time delay is less than 50 micro seconds.

8. A hearing aid of a type selected from the group consisting of a behind-the-ear hearing aid, an in-the-ear hearing aid and a completely-in-the-canal hearing aid, said hearing aid comprising
    a generator for generating a test stimulus signal,
    a digital signal processor adapted for processing and converting the test stimulus signal in order to output an acoustic stimulus signal, and
    a first synchronizing means for providing timing information about the outputting of the acoustic stimulus signal,
    wherein said digital signal processor is adapted to process the test stimulus signal according to an audiologic fitting prescription for an individual, in order to test the aided hearing threshold of the individual.

9. A system for determining a hearing ability of an individual, said system comprising,
    an electrophysiological instrument, said instrument having means for generating a test stimulus signal and electrophysiological response means for establishing from said individual an evoked response,
    a hearing aid of a type selected from the group consisting of a behind-the-ear hearing aid, an in-the-ear hearing aid and a completely-in-the-canal hearing aid, said hearing aid having a calibrated input adapted for receiving said test stimulus signal, and a digital signal processor for processing and converting said test stimulus signal into an acoustic stimulus signal suitable for evoking in the individual an electrophysiological response,
    wherein said hearing aid is adapted for operating with a constant time delay between receiving the test stimulus signal and outputting the acoustic stimulus signal.

10. A method for carrying out electrophysiological measurement of a hearing ability of an individual, comprising the steps of generating a trigger pulse, generating in said hearing aid, in response to said trigger pulse, a test stimulus signal and converting the test stimulus signal into an acoustic stimulus signal, wherein the time delay between the trigger pulse and the acoustic stimulus signal is essentially constant, and measuring an electrophysiological response evoked in the individual by the acoustic stimulus signal.

* * * * *